United States Patent
Sanpei

(12) 
(10) Patent No.: US 6,382,213 B1
(45) Date of Patent: May 7, 2002

(54) DEVICE FOR THE PROTECTION OF SIGHT AND HEARING

(75) Inventor: Richard Kazuhiro Sanpei, Cayucos, CA (US)

(73) Assignee: Richard Sanpei, Cayucos, CA (US)

( * ) Notice: Subject to any disclaimer, the term of this patent is extended or adjusted under 35 U.S.C. 154(b) by 0 days.

(21) Appl. No.: 09/550,586

(22) Filed: Apr. 17, 2000

(51) Int. Cl.⁷ .................................................. A61F 11/00

(52) U.S. Cl. ........................................ 128/864; 128/866

(58) Field of Search ........................ 128/846, 864–868, 128/857, 858; 2/7, 9, 10, 11, 209

(56) References Cited

U.S. PATENT DOCUMENTS

| | | | | |
|---|---|---|---|---|
| 2,946,394 A | * | 7/1960 | Smith | 128/866 |
| 3,856,007 A | * | 12/1974 | Leight | 128/866 |
| 3,943,925 A | * | 3/1976 | Leight | 128/866 |
| 5,749,373 A | * | 5/1998 | Dix | 128/866 |
| 5,806,526 A | * | 9/1998 | Rhoad | 128/866 |
| 5,809,574 A | * | 9/1998 | Falco | 2/209 |

* cited by examiner

*Primary Examiner*—Michael A. Brown

(57) ABSTRACT

A device that is used for the protection of the hearing and sight of the person wearing it. It is supported on a person's head through contact with both ear canals and the bridge of a person's nose. It is readily adjustable so as to be used by persons with differing sized heads.

19 Claims, 5 Drawing Sheets

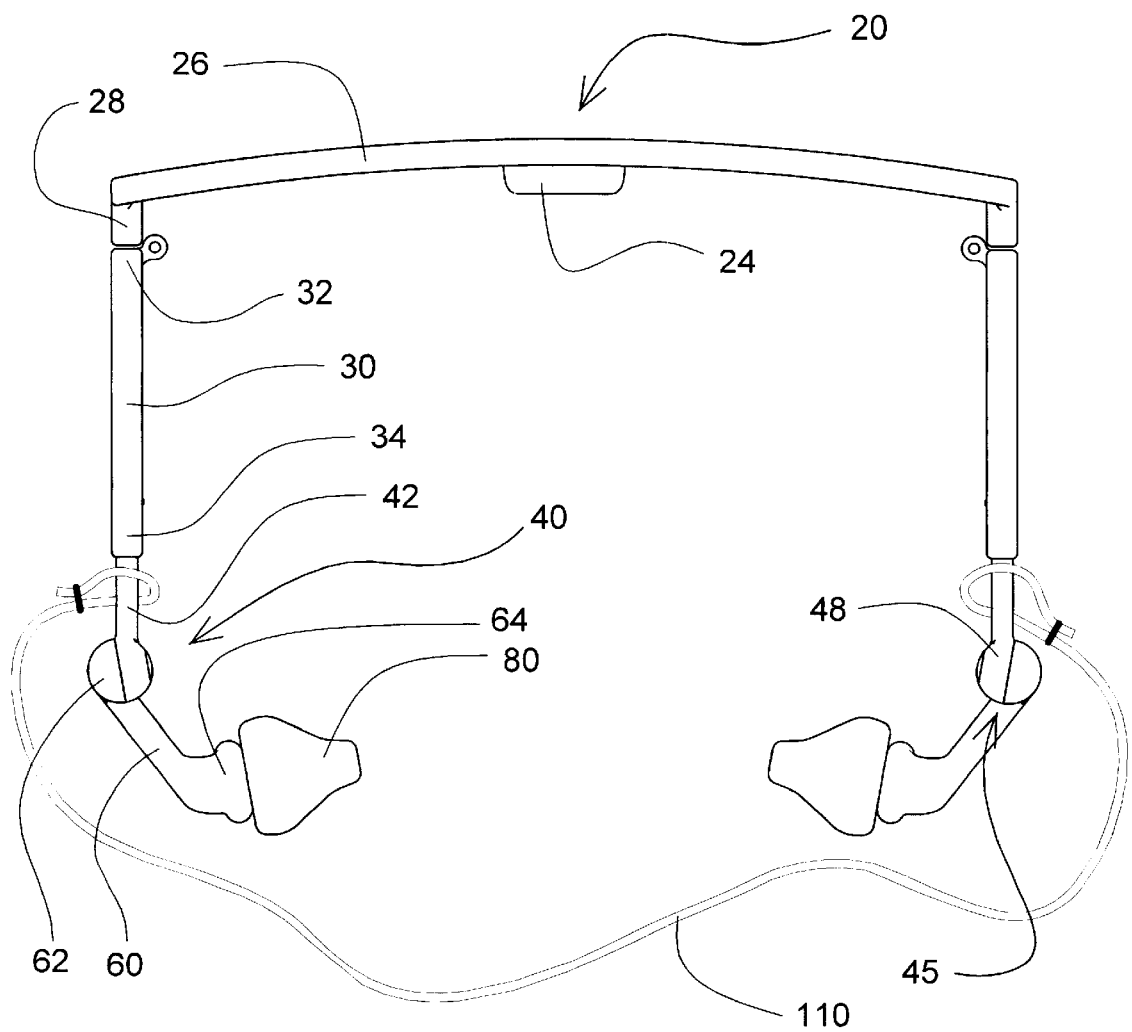

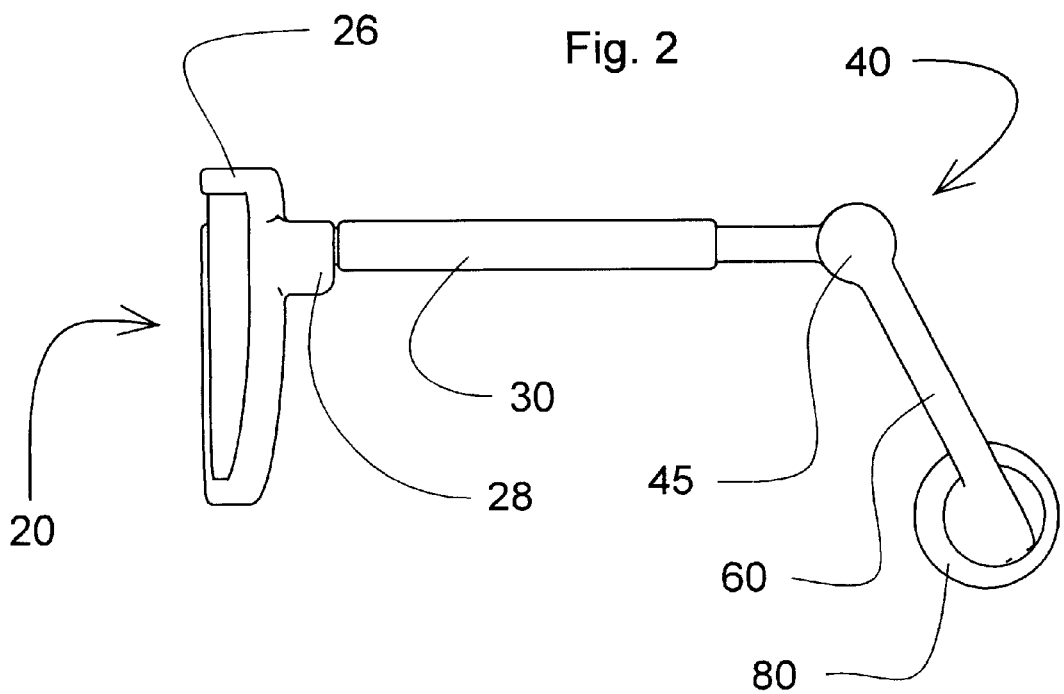
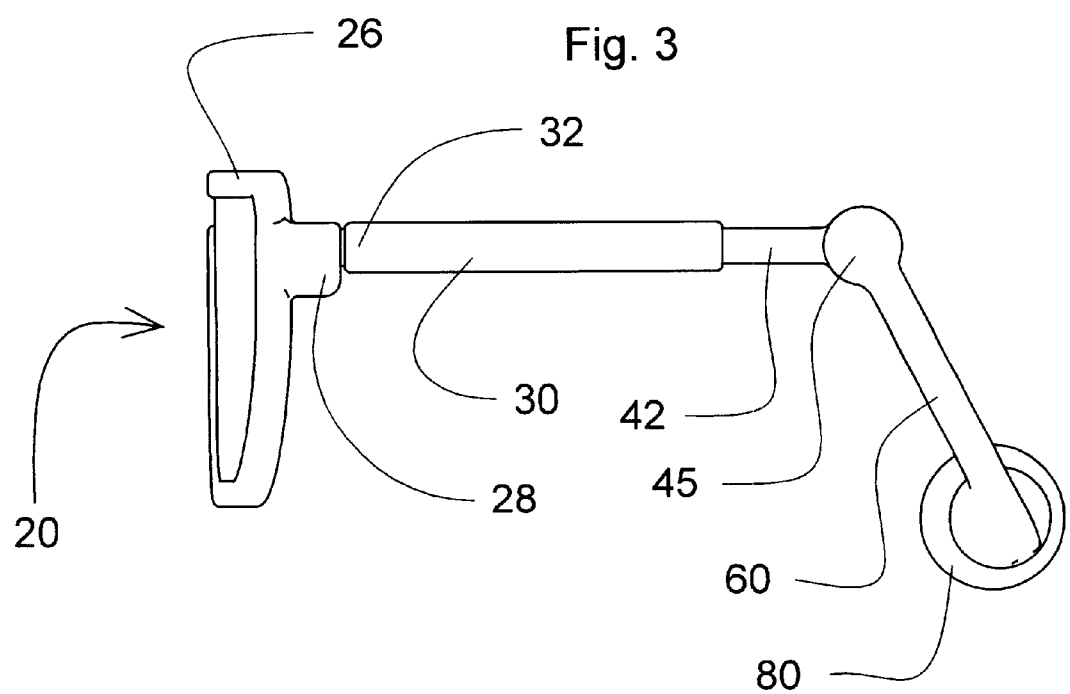

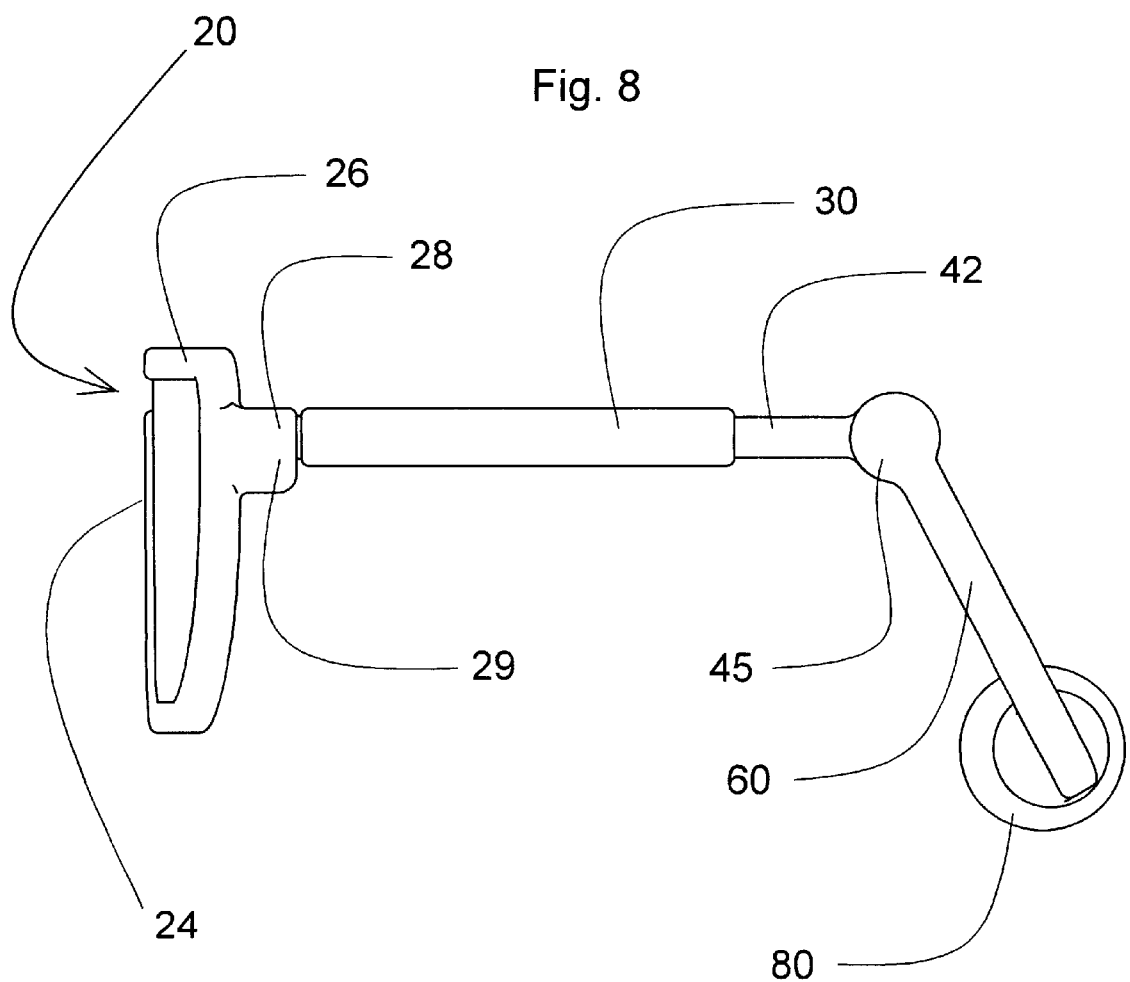

DEVICE FOR THE PROTECTION OF SIGHT AND HEARING

BACKGROUND—FIELD OF THE INVENTION

This invention relates, in general, to safety devices, and in particular, to devices which protect the eyesight and hearing of the user of the device from injury.

BACKGROUND—DESCRIPTION OF PRIOR ART

Often it is desired to protect the eyes, from flying debris, and to protect the hearing, from injury due to excessive noise. Well-known solutions to provide these protections are separate safety glasses and earplugs. Requiring separate devices for these protections creates some problems. Sometimes separate devices interfere with each other. The requirement of two separate devices requires the employee to keep track of two devices instead of one. Once the two devices are combined a problem arises in having sufficient adjustment in the single device so that the when the safety glasses are in place, the hearing protectors are lined up with the auditory canal of the ear.

Other solutions to this problem include providing safety glasses with earplugs attached in some manner. As an example, Leight, U.S. Pat. No. 3,943,925, provides a device whereby earplugs are connected to the temple bar of a pair of glasses. The problem with invention shown in the Leight patent is that the earplugs, and the section of the temple bar that bends around the ear would interfere with each other's operation. If the earplugs were adjusted so that they were snug in the wearer's ear, then most likely, the temple bar would be held out away from the head. If the temple bar is in contact with the head (especially the section that bends around the ear), then most likely, the earplugs will not be snugly fitting into the auditory canal of the wearer's ear. Other problems with the device of the Leight patent is that the sliding blocks that provide connection of the ear plugs to the temple bar, are complex, requiring other tools for their adjustment. They are also bulky.

Another solution to the problem of having to use separate devices for hearing and sight protection, has been addressed in U.S. Pat. No. 5,781,272, of Aaron Lee Bright et al. This patent shows a device that includes glasses and hearing protection. The device shows a hearing protection assembly that slips into the sleeve of the temple part. The temple part contains a pin that is inserted into holes in the leg of the hearing protection assembly. This is what holds the hearing protection assembly to the glasses. A problem with this invention is that the solution of vertical adjustment is accomplished through a complex and costly design process of including a wire into the molded S shaped part of the hearing protection assembly. Furthermore, with this device it would be difficult to maintain sufficient pressure on the earplugs, thereby providing less than optimum hearing protection.

SUMMARY

The present invention is an eye and hearing protection device. As such it comprises a pair of safety glasses, combined to a hearing protection device for each ear, and includes means for sufficient adjustment so as to be useable by most people, and also includes means to hold that adjustment once made.

OBJECTS AND ADVANTAGES

Several objects and advantages of the present invention are:

(a) to provide for the protection of both eyes and hearing for the user of the invention;

(b) to provide for sufficient adjustability so that both the safety glasses and the hearing protection devices can be positioned to be effective and comfortable;

(c) to provide means to hold sufficiently securely the conformation of the invention once the protection devices have been adjusted in relation to each other;

(d) to provide a means so that a neck strap can be usefully attached to the present invention;

(e) to make easier for a worker to retain and use the protection of both hearing and eyesight protection;

(f) to provide clearance from the ear so that a pencil can be held between the ear and the head of a worker;

(g) to provide a device that requires a worker to use hearing protection if he is to using the eyesight protection.

Still further objects and advantages will become apparent from the following description and drawings.

DRAWING FIGURES

FIG. 1 is a top view of the preferred embodiment of the eyesight and hearing safety apparatus.

FIG. 2 is a side view of the present invention.

FIG. 3 is a side view of an alternative embodiment of the present invention.

FIG. 8 is view of another embodiment of the present invention.

PREFERRED EMBODIMENT

Figure 4:
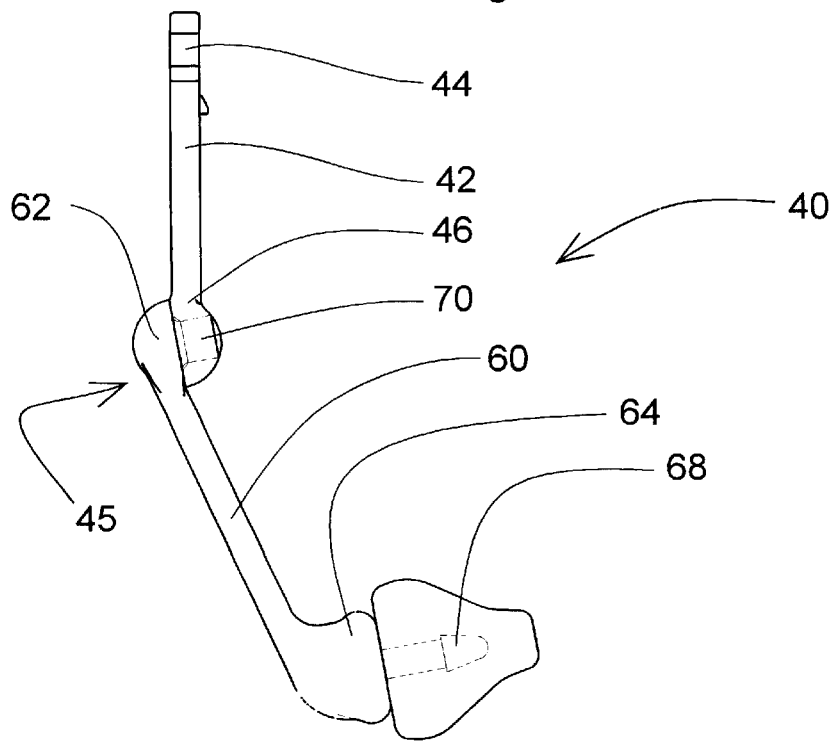
FIG. 4 is a view of the hearing protection assembly of the invention.

All the embodiments shown in FIGS. 1, 2, 3, 4, 5, 6, 7, and 8 are of an eyesight and hearing safety apparatus that protects the user's sight and hearing when worn correctly. The preferred embodiment of my invention includes a front guard portion 20, which includes a transparent panel section 22, connected to an elongated resilient member 26. The guard portion also includes a bridge portion 24, well known in the art, where the device is supported from the user's nose. An elongated resilient member 26 is connected to the top edge of the transparent panel section. At each end of the two ends of the elongated member 26 is a hinge section 28. Pivotally attached to each of these hinge sections 28 is a temple section 30. This temple section has two ends including hinged end of temple 32, and attachment tube end of the temple 34.

A hearing protection assembly 40, attaches to each temple section 30. It includes an arm member 42, a leg member 60, and an earplug 80. Arm member 42 has two ends. One end is attachment end 44, which attaches by sliding into attachment tube end of the temple 34. The opposite end is pivot end of arm 46. It is attached to pivot end of the leg 62. The opposite end of leg member 60, earplug attachment end 64, includes an earplug post 68 onto which is held earplug 80.

The arm member and leg member are connected so as to pivot rotationally around their pivoting attachment 45. They contact each other at a planar surface located on both the arm and leg member. Therefore, arm planar surface 96, is proximate leg planar surface 98 when hearing protection assembly 40 is properly assembled. A pivot post 70 protrudes substantially perpendicularly from arm planar surface 96. This pivot post 70 is inserted into a pivot hole 72 that passes at least partially through pivot end of the leg 62. The circumference of pivot post 70 away from its protrusion from the planar surface is greater then its circumference closer to the planar surface.

These surfaces, in the preferred embodiment, are knurled so as to provide resistance to movement of the arm and leg in their relationship to each other.

Figure 7:
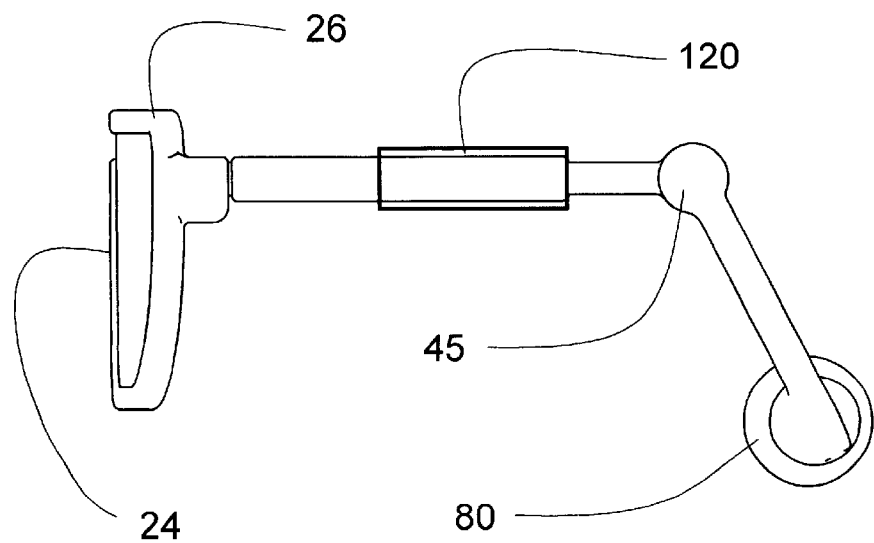
FIG. 7 is a side view of an embodiment showing the use of a length of tubing to secure the hearing protection assembly to the temple section.

The preferred embodiment also has an obstruction on arm 48 that provides a stop for the loop of the end of an elongated securing tie piece 110. FIG. 7 shows a length of resilient tubing 120 surrounding temple section 30 and arm member 42 holding them together.

While the preferred embodiment has a post protruding from the arm member and the hole into the leg member, other embodiments can have the post protruding from the leg member and the hole in the arm member. Additionally, there can be a hole into both the arm and the leg with an independent pivot pin 94 connecting the arm member to the leg member.

Another embodiment of the invention includes a resilient washer 100 between the arm planar surface 96 and the leg planar surface 98. This washer provides additional resistance to movement of the pivoting attachment.

Another embodiment, as shown in FIG. 3 of the invention shows arm member 42 hingably attached to elongated resilient member 26. In this embodiment temple section 30 is part of arm member 42. This single part is connected to leg member 60 by pivoting attachment 45 in the same way as the other embodiment.

Figure 5:
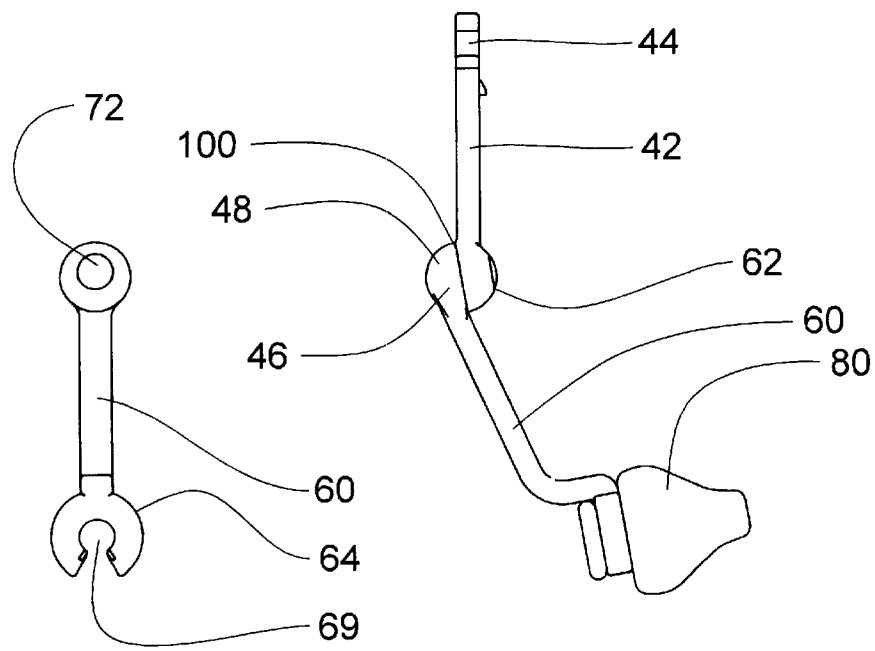
FIG. 5 is a view of an alternative embodiment of the hearing protection assembly of the invention.
Figure 6:
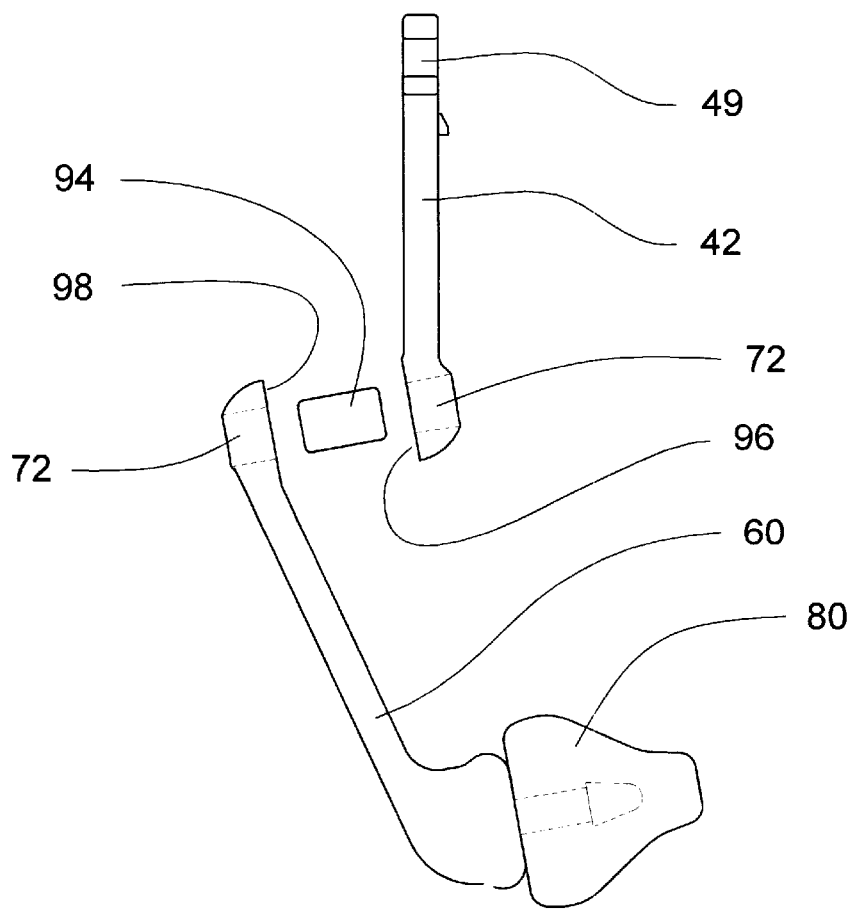
FIG. 6 is a detail of a part of the hearing protection assembly of the invention.

Another embodiment, as shown in FIG. 5, shows a partially encircled void 69 for attachment of an earplug to the leg member.

FIG. 8 shows an embodiment of the invention without the resilient elongated member attached to the transparent panel. Instead a connective piece 29 with a hinge section 28, provides for the attachment of temple section 30. This connective piece is attached to transparent panel 22 by snapping into a hole through the transparent panel, or by gluing it onto the panel. It also can be riveted or screwed onto the panel. All of these attachments are known in the art.

OPERATION

The hearing and sight protection device of the invention is put on much the same as one would wear any safety glasses. With safety glasses, however, a member is attached to temple section 30, and is placed over and behind the ear, next to the head, holding the glasses in position on the user's head. With this invention, a hearing protection assembly 40 is attached to each of temple sections 30. This assembly has attached to it an earplug 66 that is put in the user's ear. Transparent panel portion 22 is held correctly in place on the user's head when each earplug 66 is fitted in the user's ear and bridge portion 24 is resting on the user's nose. Pivoting attachment 45 allows for the adjustment to be made for individuals with different sized and shaped heads.

Hearing protection assembly 40 is attached to the glasses by sliding the end of the hearing assembly into attachment tube end of temple section 34. Hearing protection assembly 40 has two elongated members that are connected by a pivoting attachment 45. This attachment allows for adjustment so workers with differently shaped heads can use the same device.

A length of resilient tubing 120 is placed over temple section 34 and over arm member 42, covering the connection and along a portion of the length of each, holding them together.

The loop ends of an elongated securing tie piece 110 are looped over the hearing protection assembly 40 and are tightened around the arm member 42 where they are held from slipping off by the obstruction on the arm 48.

CONCLUSIONS RAMIFICATIONS AND SCOPE

Thus the reader will see that the hearing and eyesight protection device of the invention, provides an useful and economical way for a worker to be safely equipped to protect both his sight and hearing in a working situation.

While the above description contains many specificities, these should not be construed as limiting the scope of the invention but as merely providing illustrations of some of the presently preferred embodiments of this invention. For example, the illustrations of the invention show leg member 60 attached one side of arm member 42. It could be attached to the opposite side without limiting the scope of the invention.

Thus the scope of the invention should be determined by the appended claims and their legal equivalents, rather than by the examples given.

I claim:

1. An eyesight and hearing safety apparatus for use by a human being, said apparatus comprising:
   (a) a front guard portion including;
      (1) a transparent panel section, said front transparent panel section for protecting the eyesight of the human being, the transparent panel section having two ends;
      (2) a bridge portion located between said two ends that supports the transparent panel section from the nose of a user;
      (3) a hinge connection means whereby a hinge section is attached to each of the two ends of the transparent panel section,
   (b) a pair of temple sections, each said temple section having two ends, one end hingably attached to said hinge section, the opposite end of the temple section tubularly shaped,
   (c) a right and a left hearing protection assembly,
      (1) each said assembly includes an arm member, and a leg member,
      (2) each assembly includes a pivoting attachment combining said arm member and said leg member, said pivoting attachment allowing for rotational movement of the arm member and leg member around the pivoting attachment,
      (3) the arm member is shaped to slide into the tubular shaped end of the temple section,
      (4) the leg member includes an earplug attachment means whereby an earplug is attached to said attachment leg,
      (5) an obstruction on the arm member providing a stop so that an elongated securing tiepiece can be securely attached.

2. An eyesight and hearing safety apparatus of claim 1, where said earplug attachment means is an earplug post projecting from a earplug attachment end of leg.

3. An eyesight and hearing safety apparatus of claim 2 where said attachment means includes an at least partially encircled void into which the earplugs are inserted and held securely.

4. An eyesight and hearing safety apparatus of claim 1 wherein said hinge connection means includes an elongated resilient member holding along a top edge of the front transparent panel.

5. An eyesight and hearing safety apparatus of claim 1 wherein said hinge connection means includes a connective piece attached to each of said hinge two ends of the transparent panel.

6. An eyesight and hearing safety apparatus of claim 1 where a length of resilient tubing encircles the temple part and the arm member, securing their connection to each other.

7. An eyesight and hearing safety apparatus of claim 1 wherein an arm planar surface and a leg planar surface contact each other providing frictional resistance to movement.

8. An eyesight and hearing safety apparatus of claim 6 wherein a leg planar surface and as arm planar surface contain obstructions thereby providing increased resistance to movement.

9. An eyesight and hearing safety apparatus of claim 1, wherein an arm planar surface and a leg planar surface each contact a washer sandwiched by them, said washer providing frictional resistance to movement.

10. An eyesight and hearing safety apparatus of claim 1, wherein the arm is slidably inserted into the tubular end of said temple section.

11. An eyesight and hearing safety apparatus for use by a human being, said apparatus comprising:
   (a) a front guard portion including;
      (i) a transparent panel section, said front transparent panel section for protecting the eyesight of the human being, the transparent panel section having two ends;
      (2) a bridge portion located between said two ends that supports the transparent panel from the nose of a user,
      (3) a hinge connection means whereby a hinge section is attached to each of the two ends of the transparent panel section,
   (b) a right and a left hearing protection assembly,
      (1) each said assembly includes an arm member, and a leg member,
      (2) each assembly includes a pivoting attachment combining said arm member and said leg member, said pivoting attachment allowing for rotational movement of the arm member and leg member around the pivoting attachment,
      (3) the arm member includes a temple section that is hingably attached to the hinge section,
      (4) the leg member includes an earplug attachment means whereby an earplug is attached to said attachment leg.

12. An eyesight and hearing safety apparatus of claim 11, where said earplug attachment means is an earplug post projecting from a earplug attachment end of leg.

13. An eyesight and hearing safety apparatus of claim 11 where said attachment means includes an at least partially encircled void into which the earplugs are inserted and held securely.

14. An eyesight and hearing safety apparatus of claim 11 where an obstruction on the arm member provides a stop so that an elongated securing tiepiece can be securely attached.

15. An eyesight and hearing safety apparatus of claim 11 wherein an arm planar surface and a leg planar surface contact each other providing frictional resistance to movement.

16. An eyesight and hearing safety apparatus of claim 15 wherein said leg planar surface and said arm planar surface include obstructions thereby providing increased resistance to movement.

17. An eyesight and hearing safety apparatus of claim 11, wherein an arm planar surface and a leg planar surface each contact a washer sandwiched by them, said washer providing frictional resistance to movement.

18. An eyesight and hearing safety apparatus of claim 1 wherein said hinge connection means includes an elongated resilient member holding along a top edge of the front transparent panel section.

19. An eyesight and hearing safety apparatus of claim 1 wherein said hinge connection means includes a connective piece attached to each of said two ends of the transparent panel section.

* * * * *